US 8,198,470 B2

(12) United States Patent
Levi et al.

(10) Patent No.: US 8,198,470 B2
(45) Date of Patent: Jun. 12, 2012

(54) CRYSTALLINE FORM II OF TIGECYCLINE AND PROCESSES FOR PREPARATION THEREOF

(75) Inventors: Sigalit Levi, Modi'in (IL); Michal Rafilovich, Petach-Tikva (IL); Sofia Gorohovsky-Rosenberg, Beer-Sheva (IL); Slavik Yurkovski, Kiryat-Gat (IL); Sergei Fine, Lahavim (IL); Leonid Metsger, Beer-Sheva (IL); Evgeny Tsiperman, Be'er Sheva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 634 days.

(21) Appl. No.: 12/325,686

(22) Filed: Dec. 1, 2008

(65) Prior Publication Data

US 2010/0152142 A1    Jun. 17, 2010

Related U.S. Application Data

(63) Continuation-in-part of application No. 11/789,432, filed on Apr. 24, 2007, now Pat. No. 7,871,993.

(60) Provisional application No. 61/004,786, filed on Nov. 29, 2007, provisional application No. 60/794,763, filed on Apr. 24, 2006, provisional application No. 60/796,800, filed on May 1, 2006.

(51) Int. Cl.
| | |
|---|---|
| *C07C 43/00* | (2006.01) |
| *C07C 49/00* | (2006.01) |
| *C07C 233/01* | (2006.01) |
| *C07C 237/26* | (2006.01) |
| *A61K 31/65* | (2006.01) |
| *A61K 31/167* | (2006.01) |
| *A61P 31/00* | (2006.01) |

(52) U.S. Cl. ......... 552/205; 514/152; 514/616; 564/157

(58) Field of Classification Search .................. 514/152, 514/616; 552/205; 564/157
See application file for complete search history.

(56) References Cited

U.S. PATENT DOCUMENTS

| | | | |
|---|---|---|---|
| 2,980,584 | A | 4/1961 | Hammer et al. |
| 2,990,331 | A | 6/1961 | Neumann et al. |
| 2,997,471 | A | 8/1961 | Cheney et al. |
| 3,062,717 | A | 11/1962 | Hammer et al. |
| 3,165,531 | A | 1/1965 | Blackwood et al. |
| 3,454,697 | A | 7/1969 | Joyner et al. |
| 3,557,280 | A | 1/1971 | Weber et al. |
| 3,674,859 | A | 7/1972 | Beutel et al. |
| 3,957,980 | A | 5/1976 | Noseworthy |
| 4,018,889 | A | 4/1977 | Armstrong |
| 4,024,272 | A | 5/1977 | Rogalski et al. |
| 4,126,680 | A | 11/1978 | Armstrong |
| 5,281,628 | A | 1/1994 | Hlavka et al. |
| 5,284,963 | A | 2/1994 | Sum et al. |
| 5,401,863 | A | 3/1995 | Hlavka et al. |
| 5,494,903 | A | 2/1996 | Hlavka et al. |
| 5,495,031 | A | 2/1996 | Sum et al. |
| 5,675,030 | A | 10/1997 | Krishnan et al. |
| 6,384,221 | B1 * | 5/2002 | Thiele et al. .................. 544/281 |
| 2006/0183720 | A1 | 8/2006 | Sum et al. |
| 2006/0247181 | A1 | 11/2006 | Fawzi et al. |
| 2007/0026080 | A1 | 2/2007 | Chanana et al. |
| 2007/0049560 | A1 | 3/2007 | Krishnan et al. |
| 2007/0049561 | A1 | 3/2007 | Krishnan et al. |
| 2007/0049562 | A1 | 3/2007 | Krishnan et al. |
| 2007/0049563 | A1 | 3/2007 | Krishnan et al. |
| 2007/0123497 | A1 | 5/2007 | Krishnan et al. |

FOREIGN PATENT DOCUMENTS

| | | |
|---|---|---|
| EP | 0 535 346 | 4/1993 |
| JP | 01-029346 | 1/1989 |
| WO | WO 02/072031 | 9/2002 |
| WO | WO 2006/128150 | 11/2006 |
| WO | WO 2006/130431 | 12/2006 |
| WO | WO 2006/130501 | 12/2006 |
| WO | WO 2008/066935 | 6/2008 |
| WO | WO 2008/155405 | 12/2008 |

OTHER PUBLICATIONS

Bruttel et al. Water Determination by Karl Fischer Titration. Metrohm Monograph 8.026.5013 (Feb. 2006).*
Vippagunta et al. Crystalline Solids. Adv. Drug Del. Rev. 48, pp. 3-26 (2000).*
Measuring colour, 3rd Ed. / R.W.G. Hunt (1998).
Polymorphism in Pharmaceutical Solids, Drugs and the Pharmaceutical Sciences, vol. 95.
Anonymous, "Tygacil Scientific Discussion", EMEA 2006 http://www.infectiologie.com/site/medias/enseignment/du-lyon/Tygacil%20EPAR.pdf.
Database WPI Week 198910. Derwent Publications Ltd., London, GB: An 1989-074689, JP01029346A (Nippon Kayaku KK) Jan. 31, 1989 (Abstract).
J.Med.Chem 37: 184 (1994).
Nelson et al., "Versatile and Facile Synthesis of Diverse Semisynthetic Tetracycline Derivatives via Pd-Catalyzed Reactions", Journal of Organic Chemistry, 68: 5838-5851 (2003).
Sum et al., "Synthesis and Structure—Activity Relationship of Novel Glycylcycline Derivatives Leading to the Discovery of GAR-936," *Bioorganic & Medicinal Chemistry Letters*, 9: 1459-1462 (1999).
March's Advanced Organic Chemistry: Reactions, Mechanisms, and Structure; 5th Ed.
European Search Report for EP Application No. 11180957.0, dated Feb. 7, 2012, 4 pages.
Threlfall, Terence L., "Analysis of Organic Polymorphs: A Review", Analyst, Oct. 1995, vol. 120, pp. 2435-2460.
Bryn, Stephen, et al., "Pharmaceutical Solids: A Strategic Approach to Regulatory Considerations", Pharmaceutical Research, 1995, vol. 12, No. 7, pp. 945-954.

* cited by examiner

*Primary Examiner* — Barbara Badio
*Assistant Examiner* — Sara E Townsley
(74) *Attorney, Agent, or Firm* — Kenyon & Kenyon LLP

(57) ABSTRACT

The present invention provides processes for the preparation of crystalline forms of Tigecycline.

27 Claims, 3 Drawing Sheets a solid-state 13C NMR spectrum in the range of 90-210 ppm for tigencycline form II.

CRYSTALLINE FORM II OF TIGECYCLINE AND PROCESSES FOR PREPARATION THEREOF

CROSS REFERENCE TO RELATED APPLICATIONS

The present invention claims the benefit of the following U.S. Provisional Patent Application No. 61/004,786, filed Nov. 29, 2007. The present application is also a Continuation-in-Part application from U.S. patent application Ser. No. 11/789,432, filed Apr. 24, 2007 now U.S. Pat No. 7,871,993, which claims the benefit U.S. Provisional Patent Applications Nos. 60/794,763 filed Apr. 24, 2006; and 60/796,800 filed May 1, 2006. The contents of these applications are incorporated herein by reference.

FIELD OF THE INVENTION

The present invention relates to methods for the preparation of crystalline form II of tigecycline 4 S,4a5,5aR,12a5)-9-(2-(tert-butylamino)acetamido)-4,7-bis(dimethylamino)-1,4,4a,5,5a,6,11,12a-octahydro-3,10,12,12a-tetrahydroxy-1,1'-dioxo-2-naphthacenecarboxamide.

BACKGROUND OF THE INVENTION

Tigecycline (CAS 220620-09-7), (4S,4a5,5aR,12a5)-9-(2-(tert-butylamino)acetamido)-4,7-bis(dimethylamino)-1,4,4a,5,5a,6,11,12a-octahydro-3,10,12,12a-tetrahydroxy-1,1'-dioxo-2-naphthacenecarboxamide, is the first drug of a new generation of tetracycline antibiotics called glycylcyclines. Tigecycline has a wider range of bioactivity than the parent tetracycline and its analogues discovered so far, and it may be administrated less frequently and/or in lower doses.

Tigecycline has been introduced and marketed by Wyeth under the brand name TYGACIL® and it is especially indicated against acute lethal infections caused by Gram-negative bacteria. TYGACIL® is marketed as lyophilized powder or cake for intravenous injection and the drug substance does not contain excipients or preservatives.

Tigecycline has the following structure:

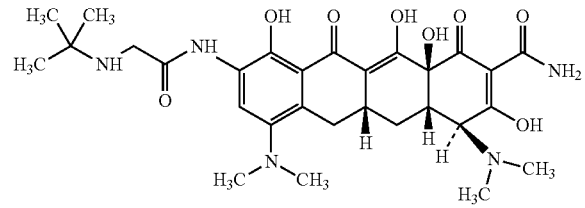

Tigecycline: $C_{29}H_{39}N_5O_8$
MW: 585.65 g/mol and was described in U.S. Pat. Nos. 5,494,903 and 5,284,963. U.S. Pat. No. 5,675,030 describes a specific method for obtaining solid Tigecycline by evaporation from a dichloromethane solution. The Tigecycline obtained from this method is amorphous. United States Publication No. 2007/0123497 describes crystalline forms of tigecycline and processes for the preparation thereof.

WO 08/066,935, describes various crystalline forms of tigecycline and processes for the preparation, and which is incorporated herein by reference.

WO 2007/127292, describes crystalline forms I and II of tigecycline, and which is incorporated herein by reference in its entirety.

The present invention relates to the solid state physical properties of tigecycline and processes preparing such tigecycline. These properties can be influenced by controlling the conditions under which tigecycline is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to thermal behavior different from that of the amorphous material or another polymorphic form. Thermal behavior is measured in the laboratory by such techniques as capillary melting point, thermogravimetric analysis ("TGA"), and differential scanning calorimetry ("DSC") and can be used to distinguish some polymorphic forms from others. A particular polymorphic form can also give rise to distinct spectroscopic properties that can be detectable by powder x-ray crystallography, solid state $^{13}$C NMR spectrometry, and infrared spectrometry.

Generally, the crystalline solid has improved chemical and physical stability over the amorphous form, and forms with low crystallinity. They can also exhibit improved hygroscopicity, bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Additionally, new processes for preparing such polymorphic forms of tigecycline may provide more efficient and economical methods, possibly increasing the yield or purity of the polymorphic form obtained. There is a need in the art for processes preparing crystalline Tigecycline and polymorphic forms thereof.

SUMMARY OF THE INVENTION

The present invention provides methods for preparation of crystalline tigecycline forms I and II.

The present invention provides crystalline tigecycline form II, characterized by data selected from the group consisting of: a powder XRD pattern with peaks at about 9.5, 9.8, 18.1, 20.2 and 21.6±0.2 degrees two-theta; a solid-state $^{13}$C NMR spectrum with signals at about 197.9, 149.1, 143.9, 115.2, and 106.0±0.2 ppm; a solid-state 13C NMR spectrum having chemical shift differences between the signal exhibiting the lowest chemical shift and another in the chemical shift range of 90 to 210 ppm of about 98.1, 49.3, 44.1, 15.4, and 6.2±0.1 ppm; a solid-state 13C NMR spectrum depicted in FIG. 2; and a solid-state 13C NMR spectrum depicted in FIG. 3. The signal exhibiting the lowest chemical shift in the chemical shift range of 90 to 210 ppm is, typically, at about 99.8±1 ppm.

The present invention provides a process for the preparation of tigecycline form I comprising: providing a solution of tigecycline in dichloromethane (DCM), performing a solvent exchange of DCM with a $C_3$-$C_6$ ester, preferably methyl acetate or ethyl acetate, to obtain a suspension, and cooling the suspension to obtain tigecycline form I.

The process above, for obtaining tigecycline form I, may further comprise slurrying tigecycline form I with a solvent selected from the group consisting of: acetonitrile and a $C_3$-$C_6$ ketone to obtain crystalline tigecycline form II.

The present invention further provides a process for the preparation of crystalline tigecycline form II comprising: providing a solution of tigecycline in dichloromethane (DCM), performing a solvent exchange of DCM with a solvent selected from the group consisting of: acetonitrile and a $C_3$-$C_6$ ketone to obtain a suspension and cooling the suspension to obtain tigecycline form II The present invention provides crystalline tigecycline form II, having a water content of more than about 1.2% by weight, preferably from about 1.2% to about 3.0% by weight, more preferably from about 1.3% to about 2.0% by weight, as measured by Karl Fisher.

The present invention further provides a process for preparing crystalline tigecycline form II, having water content of more than 1.2% by weight comprising: exposing tigecycline form II at room temperature to a humid environment for a sufficient duration of time.

DETAILED DESCRIPTION OF THE INVENTION

The present invention provides methods for preparation of crystalline tigecycline forms I and II.

As used herein the term "crystalline tigecycline form I" refers to a crystalline tigecycline characterized by powder x-ray diffraction reflections at about 4.2, 9.1, 11.4, 14.0, and 15.7±0.2 degrees two-theta and may be further characterized by powder x-ray diffraction reflections at about 8.3, 16.6, 18.1, 21.0, and 21.7±0.2 degrees two-theta.

As used herein the term "wet material" refers to a solid state of tigecycline that is surrounded by a certain amount of solvent molecules which can be readily removed by for example drying, evaporating or sublimating the solvent molecules.

As used herein, "room temperature" means a temperature of about 15° C. to about 35° C. Preferably, "room temperature" is about 20° C. to about 25° C.

As used herein, the term "air-drying" refers to drying material exposed to air at room temperature. Typically, the air-drying is performed under reduced pressure after filteration, to remove additional molecules of solvent from the material.

Figure 2:
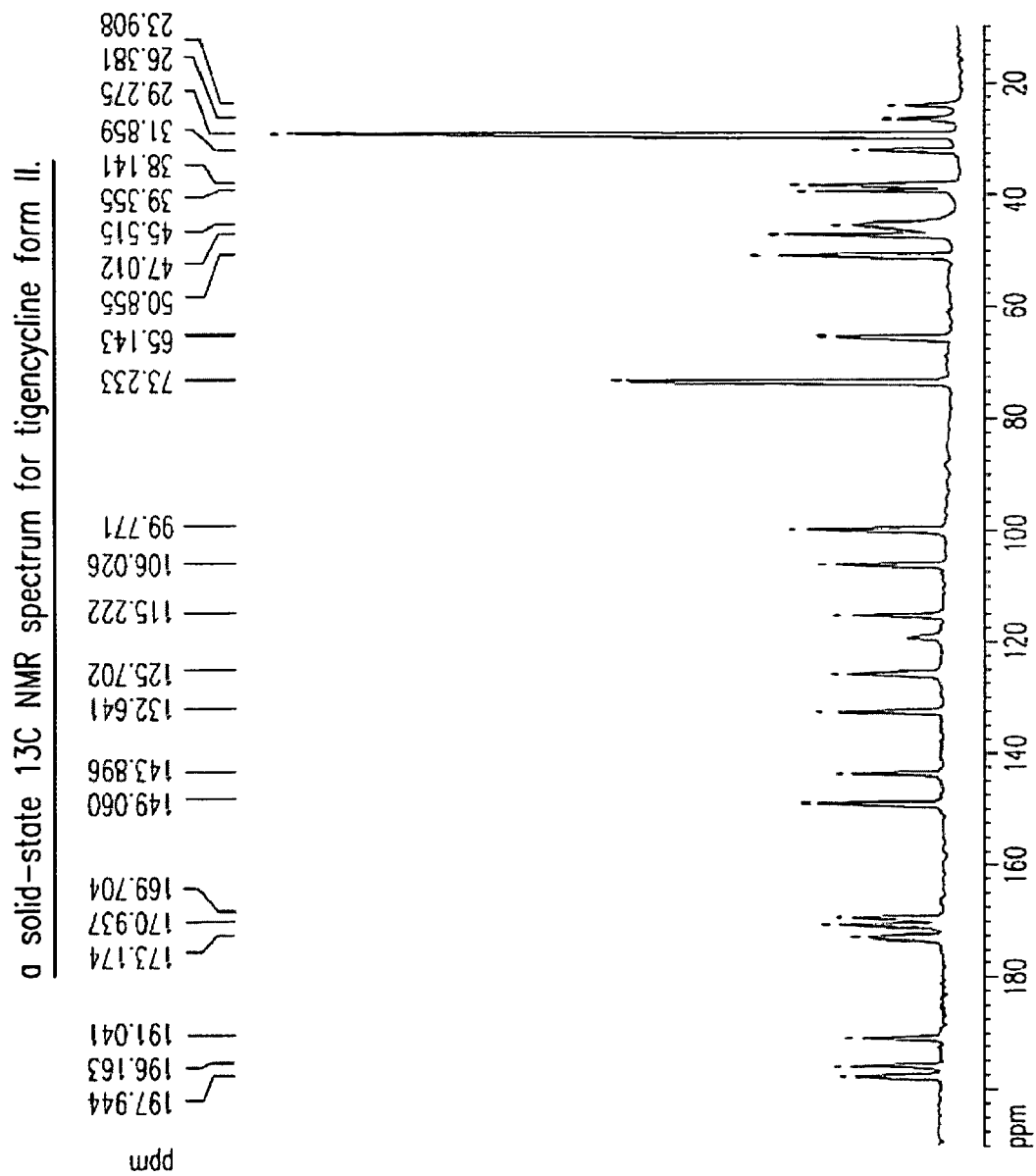
FIG. 2 illustrates a solid-state 13C NMR spectrum for tigecycline form II.
Figure 3:
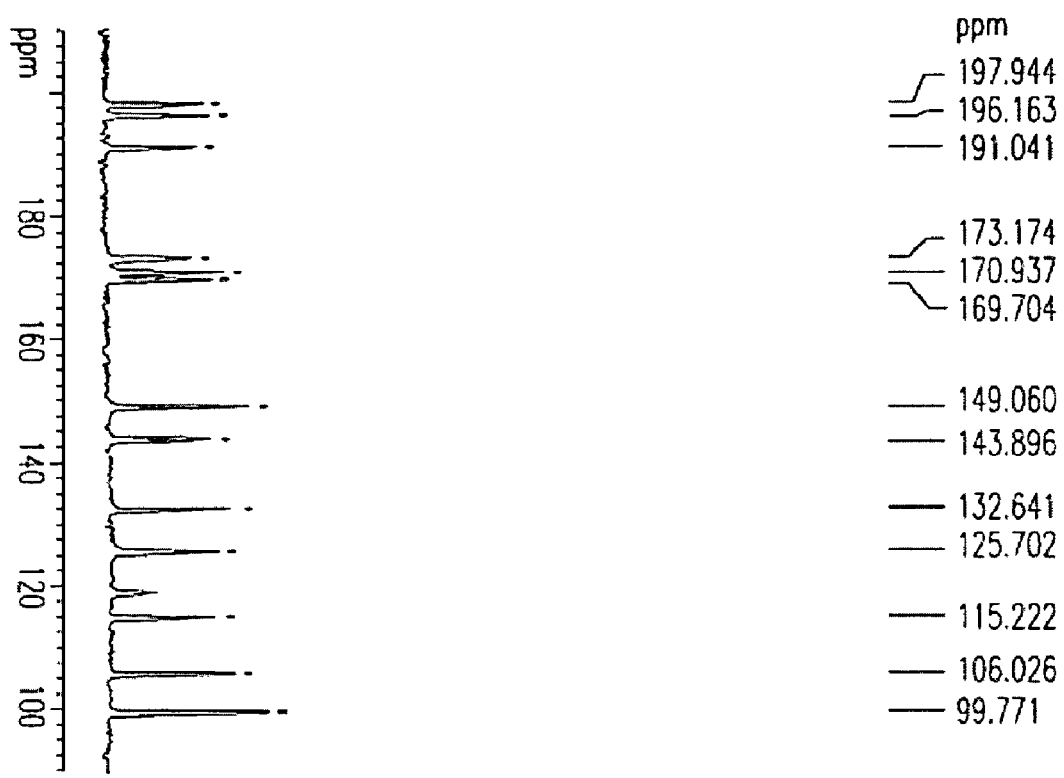
FIG. 3 illustrates a solid-state 13C NMR spectrum in the range of 90 to 210 ppm for tigecycline form II.

The present invention provides crystalline tigecycline form II, characterized by data selected from the group consisting of: a powder XRD pattern with peaks at about 9.5, 9.8, 18.1, 20.2 and 21.6±0.2 degrees two-theta; a solid-state 13C NMR spectrum with signals at about 197.9, 149.1, 143.9, 115.2, and 106.0±0.2 ppm; a solid-state 13C NMR spectrum having chemical shift differences between the signal exhibiting the lowest chemical shift and another in the chemical shift range of 90 to 210 ppm of about 98.1, 49.3, 44.1, 15.4, and 6.2±0.1 ppm; a solid-state $^{13}$C NMR spectrum depicted in FIG. 2; and a solid-state 13C NMR spectrum depicted in FIG. 3. The signal exhibiting the lowest chemical shift in the chemical shift range of 90 to 210 ppm is, typically, at about 99.8±1 ppm.

The present invention provides a process for the preparation of tigecycline form I comprising: providing a solution of tigecycline in dichloromethane (DCM), performing a solvent exchange of DCM with a $C_3$-$C_6$ ester, preferably methyl acetate or ethyl acetate, to obtain a suspension, and cooling the suspension to obtain tigecycline form I.

The process above, for obtaining tigecycline form I may further comprise slurrying tigecycline form I with a solvent selected from the group consisting of: acetonitrile and a $C_3$-$C_6$ ketone to obtain crystalline tigecycline form II.

The obtained crystalline tigecycline form II may be further dried.

Preferably the solvent exchange is performed with ethyl acetate. Preferably, cooling is performed for about 15 minutes to about 60 minutes, preferably for about 30 minutes, to a temperature of about −5° C. to about 10° C., preferably to about 0-5° C.

The solution of tigecycline in dichloromethane (DCM) used as starting material may be obtained in any method known in the art, such as described in example 6.

As used herein, "solvent exchange" refers to the process of adding a first volume of solvent to the mixture of tigecycline in DCM, concentrating the mixture, adding a second volume of solvent to the mixture and concentrating the mixture once again. Concentrating of the mixture is preferably performed by evaporation under reduced pressure.

Slurrying is performed at about room temperature for a period of about 8 to about 16 hours, more preferably about 12 hours. Preferably, slurrying is performed with acetone or acetonitrile. Filtration may also be performed, prior to the drying, using any conventional method such as for example by vacuum filtration. Drying is preferably performed under a vacuum at about 50° C. to about 80° C., most preferably at about 60-70° C., for a period of about 3-120 hrs, preferably 3-24 hours, most preferably 3-9 hours.

In a specific embodiment the invention provides a process for the preparation of crystalline tigecycline form II comprising: providing a solution of tigecycline in dichloromethane (DCM), performing a solvent exchange of DCM with ethyl acetate to obtain a suspension, cooling the suspension to about −5° C. to about 10° C., preferably to about 0-5° C., for about 15-60 minutes, preferably about 30 minutes to obtain tigecycline form I, slurrying the obtained tigecycline form I with acetone or acetonitrile to obtain tigecycline form II and drying the obtained tigecycline form II at about 50° C.-80° C., preferably at about 60° C.-70° C., for about 3-120 hours.

Preferably, when acetone is used as a solvent, and the amount of crystalline tigecycline form I starting material is about 1 Kg or more, the solvent is heated to reflux prior to combining it with form I. The mixture can be further cooled to obtain form II.

The present invention further provides a process for the preparation of crystalline tigecycline form II comprising: providing a solution of tigecycline in dichloromethane (DCM), performing a solvent exchange of DCM with a solvent selected from the group consisting of: acetonitrile and a $C_3$-$C_6$ ketone to obtain a suspension and cooling the suspension to obtain tigecycline form II.

The obtained crystalline tigecycline form II may be further dried.

Preferably, the solvent exchange is performed with acetone or acetonitrile, and cooling is performed for about 15-90 minutes, preferably about 30-60 minutes, to a temperature of about −5° C. to about 10° C., preferably about 0-5° C. Filtration may be performed prior to drying by any conventional method such as for example by vacuum filtration. Drying is preferably performed under a vacuum at about 50° C. to about 80° C., most preferably at about 60-70° C., for a period of about 3-120 hrs, preferably 3-24 hours, most preferably 3-9 hours.

In a specific embodiment, the present invention provides a process for the preparation of crystalline tigecycline form II comprising: providing a solution of tigecycline in dichloromethane (DCM), performing a solvent exchange of DCM with acetonitrile to obtain a suspension, cooling the suspension to about −5° C. to about 10° C., preferably to about 0-5° C., for about 30-90 minutes, preferably about 60 minutes, to obtain tigecycline form II and drying the obtained tigecycline form II at about 50° C. to about 80° C., preferably at about 60° C., for about 12 hours.

In another specific embodiment, the present invention provides a process for the preparation of crystalline tigecycline form II comprising: providing a solution of tigecycline in dichloromethane (DCM), performing a solvent exchange of DCM with acetone to obtain a suspension, cooling the suspension to about −5° C. to about 10° C., preferably to about 0-5° C., for about 15-60 minutes, preferably about 30 minutes, to obtain tigecycline form II, and drying the obtained tigecycline form II at about 50° C. to about 80° C., preferably at about 60° C., for about 12 hours.

The present invention provides crystalline tigecycline form II, having water content of more than 1.2% by weight, preferably from about 1.2% to about 3% by weight, more preferably from about 1.3% to about 2.0% by weight, as measured by Karl Fisher.

In another embodiment, the present invention provides a process for preparing a crystalline tigecycline form II, having water content of more than 1.2% by weight comprising: exposing tigecycline form II at room temperature, preferably at about 20° C. to about 25° C., to a humid environment for a sufficient duration of time.

The exposed sample is tigecycline form II as analyzed by XRD. Preferably, the water content of the exposed form II, as measured by KF, is of about 1.2-3.0% by weight, more preferably about 1.3-2.0% by weight, most preferably about 2.0% by weight.

Preferably the humid environment has a relative humidity of about 40%-80%, most preferably of about 80%.

A sufficient duration of time of exposing crystalline tigecycline form II to a humid environment may be about 4 to about 14 days.

In another aspect of the present invention, the present invention provides a pharmaceutical formulation comprising crystalline Tigecycline form II of the present invention. This pharmaceutical composition may additionally comprise at least one pharmaceutically acceptable excipient In another aspect of the present invention, the present invention provides a pharmaceutical composition comprising crystalline Tigecycline form II of the present invention made by the processes of the present invention, and one or more pharmaceutically acceptable excipients.

The present invention further encompasses a process for preparing a pharmaceutical formulation comprising combining crystalline Tigecycline form II of the present invention, with at least one pharmaceutically acceptable excipient.

The present invention further provides for the use of a crystalline Tigecycline form, such as one of the crystalline forms of the present invention, for the manufacture of a pharmaceutical composition for the treatment of infections, including bacterial infections, Gram-negative bacterial infections, and lethal infections.

Pharmaceutical formulations of the present invention contain at least one of the crystalline Tigecycline forms of the present invention. In addition to the crystalline Tigecycline, the pharmaceutical formulations of the present invention can contain one or more excipients. Excipients including disintegrants, glidants, binders, diluents, lubricants, flavoring agents and colorants, are added to the formulation for a variety of purposes. In such pharmaceutical compositions of the present invention wherein the composition is in liquid form the active pharmaceutical ingredient Tigecycline is suspended and any other solid excipients are dissolved or suspended in a liquid carrier such as water, vegetable oil, alcohol, polyethylene glycol, propylene glycol, or glycerin. These liquid pharmaceutical compositions can also contain emulsifying agents, viscosity enhancing agents and/or buffers.

Dosage forms of the pharmaceutical compositions of the present invention include solid dosage forms like tablets, powders, capsules, suppositories, sachets, troches, and lozenges, as well as liquid syrups, suspensions, and elixirs. The active pharmaceutical ingredient, Tigecycline, and excipients can be formulated into compositions and dosage forms according to methods known in the art, such as those using for example wet granulation, dry granulation or direct compression processes.

The present invention also provides methods of treating infections in mammals, preferably humans, by administering a therapeutically effective amount of a crystalline form of Tigecycline, as disclosed herein.

Having described the invention, the invention is further illustrated by the following non-limiting examples. Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. All references mentioned herein are incorporated in their entirety.

EXAMPLES

X-Ray powder diffraction data were obtained by using methods known in the art, using a SCINTAG powder X-Ray diffractometer model X'TRA equipped with a solid-state detector. A Copper radiation of 1.5418 Å was used. A round aluminum sample holder with zero background was used. The scanning parameters included: range: 2° to 40° 2θ; scan mode: continuous scan; step size: 0.05°. All peak positions are within ±0.2 degrees two theta.

Example 1

Preparation of Tigecycline Form II (from Acetonitrile)

1 L of Tigecycline solution in dichloromethane (about 14 g of the material) was mixed with 165 ml of ethyl acetate and concentrated to about 80 ml. 330 ml of ethyl acetate were added to the obtained concentrate and concentrated again to about 80 ml, cooled at 0-5° C. for about 30 min and filtered. The orange solid material thus obtained (tigecycline form I) was mixed with 140 ml of acetonitrile at 20-25° C. overnight, whereupon a yellow solid formed. This solid was filtered and air-dried to afford 15.6 g of Tigecycline form II. The tigecycline was dried at 60-70° C. during 3-120 hours under vacuum to obtain tigecycline form II (as analyzed according to PXRD).

Tigecycline form II thus prepared has water content, as measured by KF, of about 0.6% by weight.

Example 2

Preparation of Tigecycline Form II by Solvent Exchange (from Acetonitrile)

400 ml of Tigecycline solution in dichloromethane (about 5.6 g of the material) was mixed with 68 ml of acetonitrile and concentrated to about 35 ml. 136 ml of acetonitrile were added to the obtained concentrate and concentrated again to about 35 ml, cooled at 0-5° C. for about 1 hour, whereupon a yellow solid formed. This solid was filtered, washed with cold acetonitrile and air-dried. The wet material (tigecycline form II) was dried at 60° C. over night under vacuum to obtain 3.62 g tigecycline form II (as analyzed according to PXRD).

Tigecycline form II thus prepared has water content, as measured by KF, of about 0.4% by weight.

Example 3

Preparation of Tigecycline Form II (from Acetone)

1 L of Tigecycline solution in dichloromethane (about 14 g of the material) was mixed with 165 ml of ethyl acetate and concentrated to about 80 ml. 330 ml of ethyl acetate were added to the obtained concentrate and concentrated again to about 80 ml, cooled at 0-5° C. for about half an hour and filtered. The orange solid material thus obtained (tigecycline form I) was mixed with 138 ml of acetone at 20-25° C. overnight, whereupon a yellow solid formed. This solid was filtered and air-dried to afford 12.14 g of Tigecycline form II. The obtained wet material was dried at 60-70° C. during 3-120 hrs under vacuum to obtain tigecycline form II (as analyzed according to PXRD).

Tigecycline form II thus prepared has water content, as measured by KF, of about 0.9% by weight.

Example 4

Preparation of Tigecycline Form II by Solvent Exchange (from Acetone)

700 ml of Tigecycline solution in dichloromethane (about 10 g of the material) was mixed with 100 ml of acetone and concentrated to about 50 ml. 200 ml of acetone were added to the obtained concentrate, concentrated again to about 30 ml to obtain strong yellow precipitation. 20 ml of acetone were added to the slurry. It was cooled to 0-5° C. for about half an hour, whereupon a yellow solid formed. This solid was filtered, washed with cold acetone and air-dried. The wet material (tigecycline form II) was dried at 60° C. during overnight under vacuum to obtain 4.0 g tigecycline form II (as analyzed according to PXRD).

Tigecycline form II thus prepared has water content, as measured by KF, of about 1.2% by weight.

Example 5

Preparation of Tigecycline form II having Water Content of 2%

Tigecycline form II was exposed to 80% relative humidity (RH) for 11 days at room temperature. According to XRD, the exposed sample is form II, with water content, as measured by KF, of about 2.0% by weight.

Example 6

Preparation of a Solution of Tigecycline in DCM 9-chloroacetamidominocycline free acid was mixed with an excess of t-butylamine, which serves also as a solvent, and 10% w/w of sodium iodide and the resulted mixture was stirred at ambient temperature overnight. Upon completion of the reaction the excessive amine was evaporated to dryness and the residue was covered with 100 ml of water. The resulted mixture was adjusted at pH 5 and extracted with dichloromethane several times to remove most of the impurities. The aqueous phase was then adjusted at pH ~7.2 and extracted with dichloromethane several more times.

Figure 1:
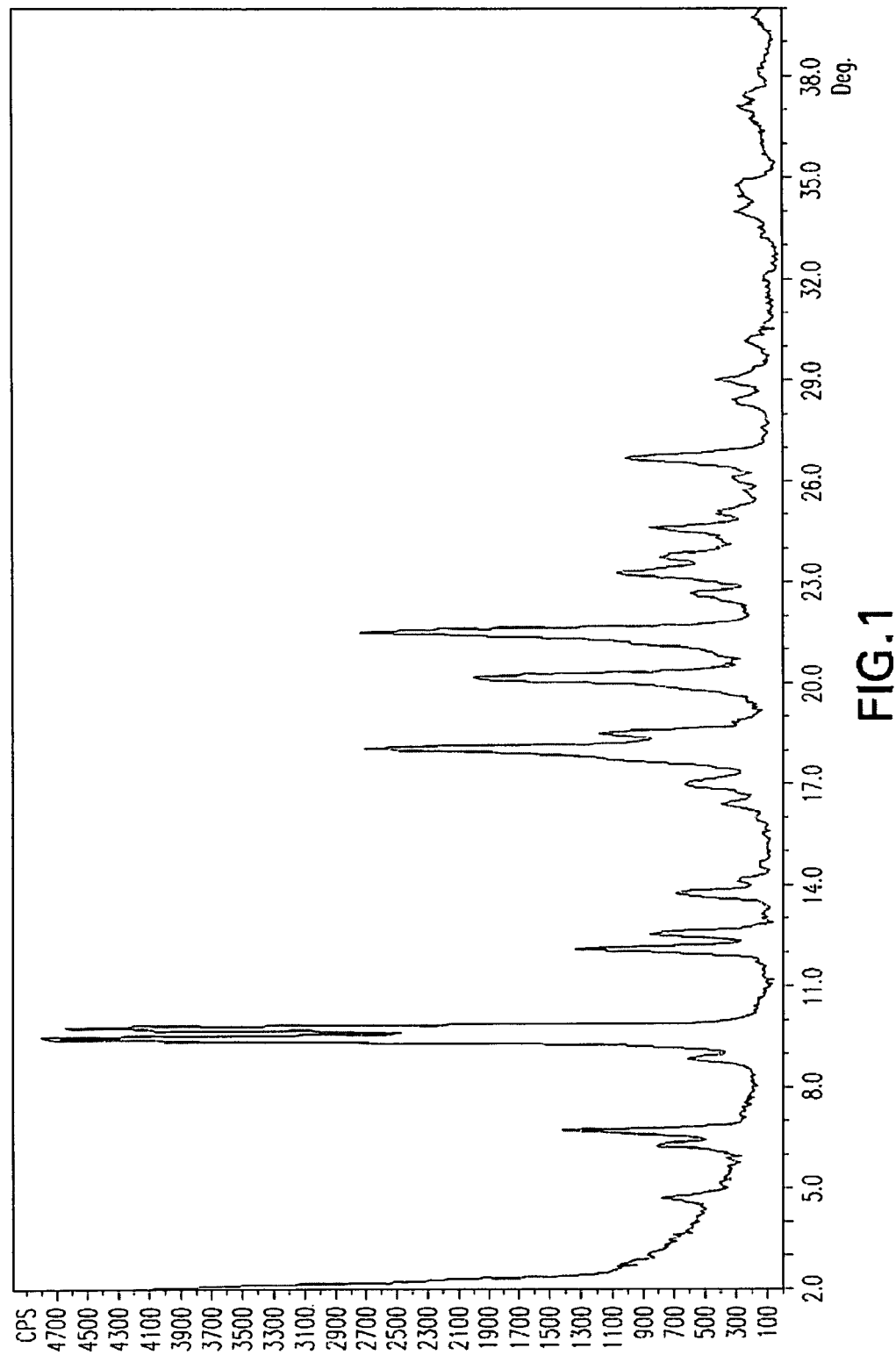
FIG. 1 illustrates a powder X-ray diffraction pattern for tigecycline form II.

The invention claimed is:

1. A crystalline tigecycline form II, characterized by data selected from the group consisting of: a powder XRD pattern with peaks at 9.5, 9.8, 18.1, 20.2 and 21.6±0.2 degrees two-theta; a powder XRD spectrum as depicted in FIG. 1; a solid-state $^{13}C$ NMR spectrum with signals at 197.9, 149.1, 143.9, 115.2, and 106.0±0.2 ppm; a solid-state $^{13}C$ NMR spectrum having chemical shift differences between the signal exhibiting the lowest chemical shift and another in the chemical shift range of 90 to 210 ppm of 98.1, 49.3, 44.1, 15.4, and 6.2±0.1 ppm wherein the signal exhibiting the lowest chemical shift in the chemical shift range of 90 to 210 ppm is at 99.8±1 ppm; a solid-state $^{13}C$ NMR spectrum depicted in FIG. 2; and a solid-state $^{13}C$ NMR spectrum depicted in FIG. 3.

2. The crystalline tigecycline of claim 1, further comprising water at an amount of more than 1.2% by weight as measured by Karl Fisher (KF).

3. The crystalline tigecycline of claim 1, having a water content of about 1.2% to about 3.0% by weight as measured by KF.

4. The crystalline tigecycline of claim 3, having a water content of about 1.3% to about 2.0% by weight as measured by KF.

5. A process of preparing crystalline tigecycline form II of claim 1 comprising: preparing crystalline tigecycline form I, characterized by a powder XRD pattern with peaks at 4.2, 9.1, 11.4, 14.0, and 15.7±0.2 degrees two-theta, comprising:
 a) providing a solution of tigecycline in dichloromethane (DCM);
 b) performing a solvent exchange of DCM with a C3-C6 ester to obtain a suspension; and
 c) cooling the suspension to obtain crystalline tigecycline form I;
 and slurrying said crystalline tigecycline form I with a solvent selected from the group consisting of acetonitrile and a C3-C6 ketone to obtain crystalline tigecycline form II.

6. The process of claim 5, further comprising drying the crystalline tigecycline form II under a vacuum at 50° C. to about 80° C. for a period of about 3-120 hours.

7. The process of claim 6, wherein the period is about 3-9 hours.

8. The process of claim 5, wherein slurrying is performed at about room temperature for a period of about 8 to about 16 hours.

9. The process of claim 8, wherein slurrying is performed at about 20-25° C.

10. The process of claim 5, wherein slurrying is performed with acetone or acetonitrile.

11. A process of preparing crystalline tigecycline form II of claim 1 comprising: a) providing a solution of tigecycline in dichloromethane (DCM); b) performing a solvent exchange of DCM with a solvent selected from the group consisting of: acetonitrile and a $C_3$-$C_6$ ketone to obtain a suspension; and c) cooling the suspension to obtain crystalline tigecycline form II.

12. The process of claim 11 further comprising drying the obtained tigecycline form II under a vacuum at about 50° C. to about 80° C. for a period of about 3-120 hours.

13. The process of claim 12, wherein the period is about 3-9 hours.

14. The process of claim 12, wherein the period is about 12 hours.

15. The process of claim 11, wherein the solvent in step b) is acetonitrile or acetone.

16. The process of claim 11, wherein cooling is performed for about 15-90 minutes to a temperature of about −5° C. to about 10° C.

17. The process of claim 16 wherein the cooling is performed to a temperature of about 0° C. to about 5° C.

18. A process of preparing the crystalline tigecycline of claim 2 comprising: exposing tigecycline form II at room temperature to a humid environment for a sufficient duration of time.

19. The process of claim 18, wherein the tigecycline form II is exposed to a humid environment at a temperature of about 20° C. to about 25° C. for a period of about 4 days to about 14 days.

20. The process of claim 18, wherein the humid environment has a relative humidity about 40%-80%.

21. The process of claim 20 wherein the humid environment has a relative humidity of about 80%.

22. The process of claim 18, wherein a crystalline tigecycline having a water content of more than 1.2% by weight as measured by Karl Fisher (KF) is obtained.

23. The process of claim 18, wherein a crystalline tigecycline having a water content of about 1.2% to about 3.0% by weight as measured by Karl Fisher (KF) is obtained.

24. The process of claim 23, wherein a crystalline tigecycline having a water content of about 1.3% to about 2.0% by weight as measured by Karl Fisher (KF) is obtained.

25. A pharmaceutical formulation comprising crystalline Tigecycline form II of claim 1 and at least one pharmaceutically acceptable excipient.

26. A pharmaceutical composition comprising crystalline Tigecycline form II of claim 1 obtained by the process of claim 5, 11, or 18, and one or more pharmaceutically acceptable excipients.

27. A process for preparing a pharmaceutical formulation comprising combining crystalline Tigecycline form II of claim 1, with at least one pharmaceutically acceptable excipient.

* * * * *